United States Patent [19] [11] 4,042,170
Ekman et al. [45] Aug. 16, 1977

[54] STERILE PACKAGE

[75] Inventors: Björn Ekman; Lars Tyrefors, both of Upplands Vasby, Sweden

[73] Assignee: AB Svenska Dental Instrument, Upplands Vasby, Sweden

[21] Appl. No.: 683,621

[22] Filed: May 5, 1976

[30] Foreign Application Priority Data

May 6, 1975 Sweden .............................. 7505268

[51] Int. Cl.² ...................... B65D 31/14; B65D 19/00
[52] U.S. Cl. ..................................... 229/62.5; 150/9; 206/439; 206/459
[58] Field of Search ............... 206/438, 439, 440, 459; 229/DIG. 14, 62, 62.5; 150/9

[56] References Cited

U.S. PATENT DOCUMENTS

| 2,349,247 | 5/1944 | Coghill | 229/62 |
| 2,870,954 | 1/1959 | Kulesza | 229/62.5 |
| 2,899,347 | 8/1959 | Kindseth | 229/62 |
| 3,088,255 | 5/1963 | Griem | 206/439 |
| 3,217,871 | 11/1965 | Lee | 206/440 |
| 3,229,813 | 1/1966 | Crowe, Jr. et al. | 206/439 |
| 3,410,395 | 11/1968 | Sellers | 206/439 |
| 3,430,842 | 3/1969 | Yamaguchi | 229/62.5 |

FOREIGN PATENT DOCUMENTS

| 701,859 | 1/1965 | Canada | 229/62.5 |
| 81,829 | 10/1963 | France | 229/62.5 |
| 1,203,174 | 10/1965 | Germany | 229/62.5 |
| 1,085,027 | 7/1960 | Germany | 229/62.5 |

Primary Examiner—Stephen P. Garbe
Assistant Examiner—Bruce H. Bernstein
Attorney, Agent, or Firm—James & Franklin

[57] ABSTRACT

A sterile package of weldable plastic foil, has a sealing welding seam, joining two mutually opposite portions of said foil, interrupted by a disc shaped valve element of gas pervious material disposed between said portions and defining at least one through hole.

12 Claims, 2 Drawing Figures

STERILE PACKAGE

BACKGROUND OF THE INVENTION

In the production of sterile packages, e.g. within the field of medicine, odontology and veterinary medicine, the object or the instrument to be sterilized is usually placed in a package, whereafter the package is closed and heated. A large problem in that connection is that the package often will burst due to the overpressure which is developed during the heating.

U.S. Pat. No. 3,088,255 discloses a method of providing a bag-like package of a flexible material, said package being adapted for use in sterilization or boiling of the contents thereof. According to this method the opening of the package is closed, after the contents have been placed within the package, by a first temporary heat sealing, wherein a filter strip for the discharge of gases developed in the package is provided in the sealing. Immediately after the heat treatment of the contents of the package a second, final sealing is provided, which completely closes the filter strip, so that a hermetical package is obtained.

A disadvantage of the method according to the above patent is that the sealing process must be performed in two steps, a temporary sealing being provided before the heat treatment and a final sealing after the heat treatment. By the final sealing air is prevented from entering into the package, if the filter strip should come loose.

Another disadvantage is that the package produced according to the known method is difficult to open.

SUMMARY OF THE INVENTION

These disadvantages, among others, are eliminated by a sterile package according to the present invention, i.e., by a package of the kind mentioned above, characterized in that said valve element comprises at least one through hole, in which the welding seam between said portions is intact. Thus, one advantage of the package according to the invention is that the sealing procedure is performed in one single step. No final sealing after the heating or the heat treatment of the contents of the package is required, since the first sealing seam always will retain the valve element. In practice the valve element thus retained has proved to operate as a check valve, which does not admit air into the package.

Another advantage of the package according to the invention is that it is easier to open, since the single sealing/welding seam is interrupted by the valve element.

An additional substantial advantage of the package according to the invention is that by convenient design of the number and shape of the holes in the valve element, the strength of the sealing and the gas permeability thereof can be varied by different location of the sealing weld across the valve element. In that way the same valve element can be utilized for packages of various sizes.

A further advantage of the package according to the invention is that, since the valve element is not enclosed by a second sealing after the heat treatment it may extend outside the package, whereby text and/or marking for the identification of the contents of the package can be provided on the part of the valve element located outside the package. Thus, no marking tape or the like need be used.

Still another advantage of the package according to the invention is that the valve element can be prepared in such a way that a colour indication is obtained at a certain temperature during the heat treatment, the color indicated being visible from outside the package and indicative of whether or not the package has been sterilized.

Another advantage of the package according to the invention is that it is very simple and inexpensive to produce, on one hand because of the fact, as mentioned above, that the sealing process is simple and on the other hand because of the fact that the valve element can be produced of a low-cost material, e.g., thick filter paper having a high heat resistance.

BRIEF DESCRIPTION OF THE DRAWING

An exemplary embodiment of the invention will now be described in detail below with reference to the attached drawing, in which.

DETAILED DESCRIPTION OF THE PREFERRED EMBODIMENTS

Figure 1:
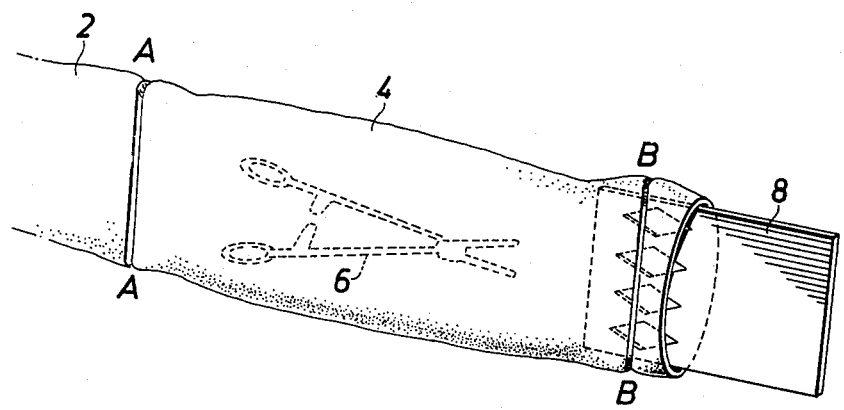
FIG. 1 illustrates how a package according to the invention is produced from a piece of a tubing of plastic material and FIG. 2 shows the sealing of the package with a preferred embodiment of the valve element.

FIG. 1 illustrates how a package 4 is produced by first providing a welding seam AA across a tubing 2 of weldable plastic material. The instrument or the object 6 to be sterilized is then introduced into the tubing through the mouth thereof, from the right hand side in FIG. 1. A valve element 8 is then inserted partially into the mouth of the tubing and a second welding seam BB is provided at the mouth across the tubing and the valve element, whereby the instrument or the object 6 to be sterilized is enclosed. The closed package 4 thus obtained is placed, e.g., in an autoclave and after the autoclave treatment it forms a sterile package.

Figure 2:
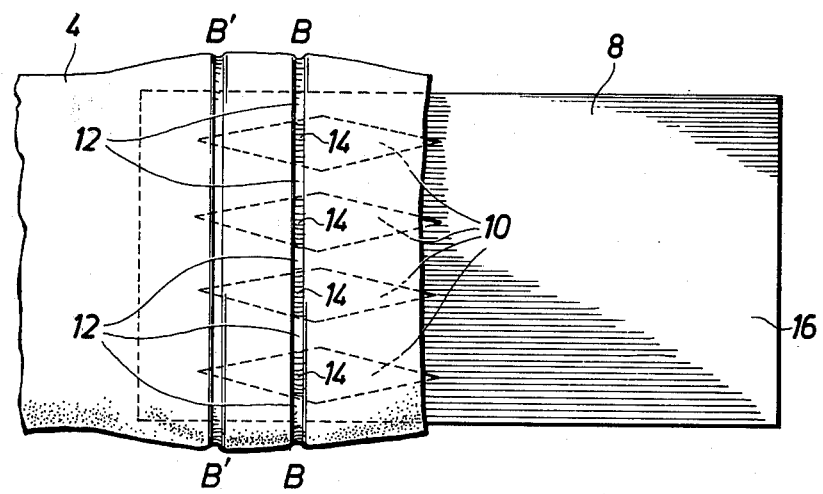

FIG. 2 illustrates the sealing of the mouth of the package 4 with a preferred embodiment of the valve element 8. The width of the valve element 8 is substantially equal to the length of the sealing seam BB (B'B'). The valve element 8 is further provided with four through holes 10, each of which having the shape of a rhomb with the shorter diagonal in parallel with the sealing seam BB (B'B'). The sealing seam BB is thereby interrupted by the portions 12 of the valve element 8, while the seam is intact in the portions 14 within the holes 10. Overpressure developed in the package during the sterilization process is discharged through the portions 12 of the valve element 8.

The gas permeability of the sealing is determined by the extension of the portions 12 of the valve element 8 in the direction of the sealing seam BB (B'B'), while the strength of the sealing (and with that the force required to open the sealing) is determined by the size of the intact portions 14 of the sealing weld BB (B'B'). With the form of the holes 10 illustrated it is thus possible to vary both the gas permeability of the sealing and the strength thereof by providing the sealing weld at different locations across the valve element 8. With a location of the sealing welding seam according to BB in FIG. 2 a strong sealing with a low gas permeability is obtained while on the contrary a location according to B'B' results in a relatively weak sealing with a high gas permeability. With such a design of the holes of the valve element that the dimensions thereof parallel with the sealing welding seam varies in the direction perpendicularly to the welding seam, it is thus possible to vary the gas flow cross section and the strength of the sealing as required, depending on the location of the sealing welding seam. A welding seam, which provides a large flow cross section, is utilized preferably in large packages having a large enclosed volume.

The disc shaped valve element 8 is preferably formed with a portion 16, protruding outside of the sealing, on which text and/or marking can be provided for the identification of the contents of the package.

Preferably the valve element is also prepared so that a colour indication is obtained at a certain temperature attained during the heat treatment. The valve element can be formed by a sheet or a board of a paper, which is not too compact, e.g., a filter paper of suitable thickness, and which has a high resistance to high temperature. The valve element, however, can also consist of other porous, gas permeable materials.

It is obvious that the holes of the valve element can be designed in a plurality of different manners and it is also possible to provide several rows of holes on the valve element, the number of holes and/or the size thereof being varied in the separate rows, so that the strength of the sealing and the gas permeability thereof is determined by that row of holes, across which the sealing weld is placed.

The valve element in the sealing of the package according to the present invention has proved to operate in practice as a check valve which will not admit air into the package.

We claim:

1. A closed sterile package of flexible weldable plastic material having at least one end construction comprising two mutually opposite portions of said plastic material, a valve element disposed between said portions, said valve element being formed of a gas pervious material and defining at least one hole through the thickness thereof, and a welding seam extending across said portions and effecting a seal between said portions at least through said hole and a seal between said portions and said valve element elsewhere.

2. The package of claim 1 wherein the dimension of said hole in the direction parallel to said seam varies in the direction perpendicular to said seam.

3. The package of claim 1 wherein said hole has the shape of a rhomb having its shorter diagonal parallel with said seam.

4. The package of claim 2 wherein said valve element extends substantially across said portions in the direction parallel to said seam.

5. The package of claim 2 wherein said valve element consists of paper having a high temperature resistance.

6. The package of claim 1 wherein said valve element extends substantially across said portions in the direction parallel to said seam.

7. The package of claim 1 wherein a portion of said valve element extends outwardly beyond said seam, whereby any text or marking for the identification of any contents of the package on said valve element portion are visible from outside of the package.

8. The package of claim 1 wherein said valve element comprises a temperature-sensitive material which undergoes a color change at a certain temperature.

9. The package of claim 1 wherein said valve element consists of paper having a high temperature resistance.

10. The package of claim 1 wherein said weldable plastic material defines a tube having said end construction adjacent at least one end thereof.

11. The package of claim 1 wherein said valve element is thin and flat.

12. The package of claim 1 wherein said valve element has at least two of said holes spaced along the dimension thereof in the direction parallel to said seam.

* * * * *